United States Patent [19]

Moser et al.

[11] Patent Number: 5,282,870
[45] Date of Patent: Feb. 1, 1994

[54] ARTIFICIAL KNEE JOINT

[75] Inventors: Walter Moser, Herrenschwanden; Roland Willi, Neftenbach, both of Switzerland

[73] Assignee: Sulzer Medizinaltechnik AG, Winterthur, Switzerland

[21] Appl. No.: 976,234

[22] Filed: Nov. 13, 1992

[30] Foreign Application Priority Data

Jan. 14, 1992 [CH] Switzerland ............... 00088/92

[51] Int. Cl.$^5$ ............................ A61F 2/38; A61F 2/30
[52] U.S. Cl. .................................. 623/20; 623/18
[58] Field of Search .................... 623/20, 16, 18

[56] References Cited

FOREIGN PATENT DOCUMENTS

| 0021421 | 1/1981 | European Pat. Off. . |
| 3314038A1 | 10/1983 | Fed. Rep. of Germany . |
| 2417293 | 9/1979 | France . |
| WO86/03117 | 6/1986 | PCT Int'l Appl. . |

*Primary Examiner*—David Isabella
*Assistant Examiner*—Debra S. Brittingham
*Attorney, Agent, or Firm*—Townsend and Townsend Khourie and Crew

[57] ABSTRACT

An artificial knee joint has a convex femoral part (1) and tibial part (2). At the femoral part (1), which has smaller radii of curvature as bending increases, the tibial part (2) performs a rolling and sliding movement, with the femoral part (1) and the tibial part (2) each comprising a lateral guide surface ($F_2$, $F_2'$) and a medial guide surface ($F_1$, $F_1'$). The medial guide surface ($F_1'$) of the tibial part (2) forms a flat guide plane, which with different flex angles, abuts cylindrical guide surfaces ($F_1$) of the femoral part (1) with line contact, while the lateral guide surface ($F_2'$) of the tibial part is trapped by the lateral condyle with different bending angles in the frontal plane in the lateral direction by line contact along circular segments having the same radius of curvature ($R_3$). The value of this same radius of curvature ($R_3$) lies between the smallest and largest flex radius ($R_n$) of the lateral condyle in the track (7).

7 Claims, 2 Drawing Sheets

ARTIFICIAL KNEE JOINT

BACKGROUND OF THE INVENTION

The invention relates to an artificial knee joint consisting of a convex femoral part and tibial part, which performs a rolling and sliding movement at the femoral part, which comprises smaller radii of curvature as flexing increases, with the femoral part and tibial part respectively comprising a lateral guide surface and a medial guide surface.

A knee joint prosthesis having a convex femoral part and having concave guide surfaces on the tibial part is shown in U.S. Pat. No. 4,568,348. This arrangement has the disadvantage that the guidance of the tibial part on a plane perpendicular to the flex axis is restricted on the femoral part by lateral guide shoulders and concave guide surfaces on the tibial part abutting lateral guide shoulders and convex guide surface of the femoral part.

SUMMARY OF THE INVENTION

The invention remedies this by emulating as far as possible the anatomical function of a natural knee joint.

The advantages of the invention lie in that the rear cruciate ligament is retained because of its anatomical function and in that, as in a natural knee, a slight torsion in the shaft axis against a constantly increasing resistance

DESCRIPTION OF THE PREFERRED EMBODIMENT

The invention shows an artificial knee joint, which consists of a convex femoral part 1 and of a tibial part 2. At the femoral part 1, which comprises smaller radii of curvature as the degree of flexure at the knee increases, the tibial part 2 performs a rolling and sliding movement. The femoral part 1 and the tibial part 2 each has a lateral guide surface $F_2$, $F_2'$ and a medial guide surface $F_1$, $F_1'$. The medial guide surface $F_1'$ of the tibial part 2 forms a flat guide plane, which at different flexure angles abuts cylindrical guide surfaces $F_1$ of the femoral part 1 with line contact, while the lateral guide surface $F_2'$ of the tibial part is trapped by the lateral condyle with different flexure angles in the frontal plane by line contact on circular segments having the same radius of curvature $R_3$ and forms a track 7 in a plane parallel to the medial guide surface $F_1'$. In this case the magnitude of this same radius of curvature $R_3$ lies between the smallest and largest bending radius $R_n$ of the lateral condyle in track 7.

Figure 1:
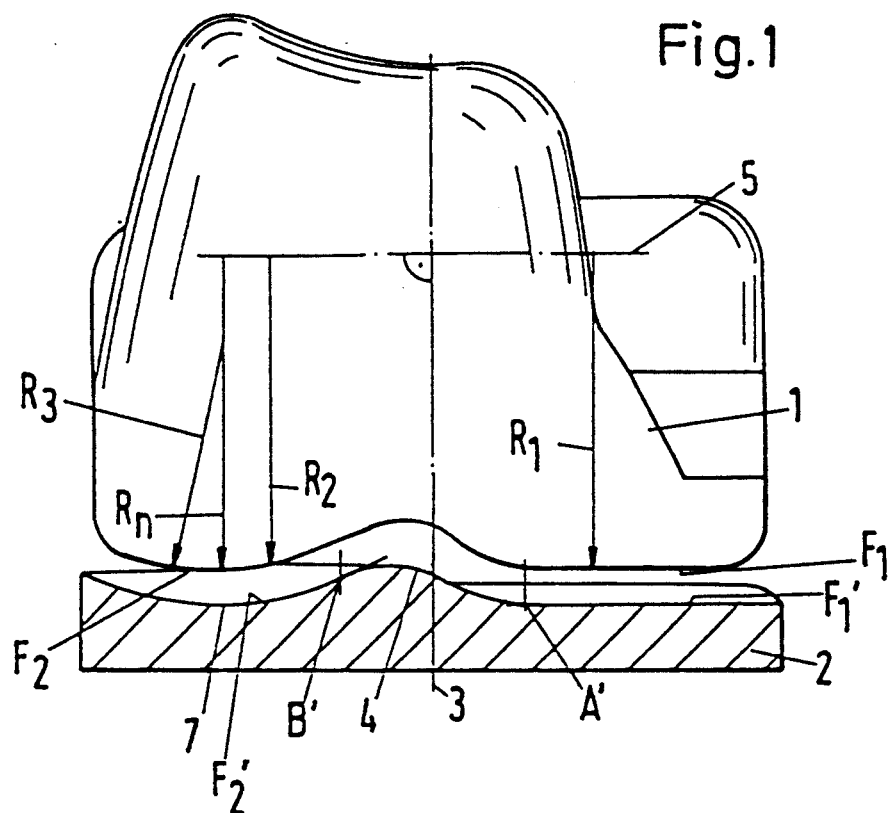
FIG. 1 is a front elevational view of a femoral part and section through the guide surfaces of the tibial part guided at the femoral part.
Figure 2:
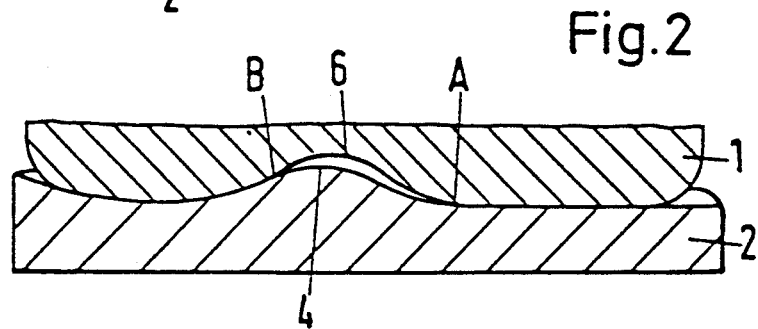
FIG. 2 is a fragmentary detail, in section, of the femoral and tibial parts shown in FIG. 1 in mutual contact
Figure 3:
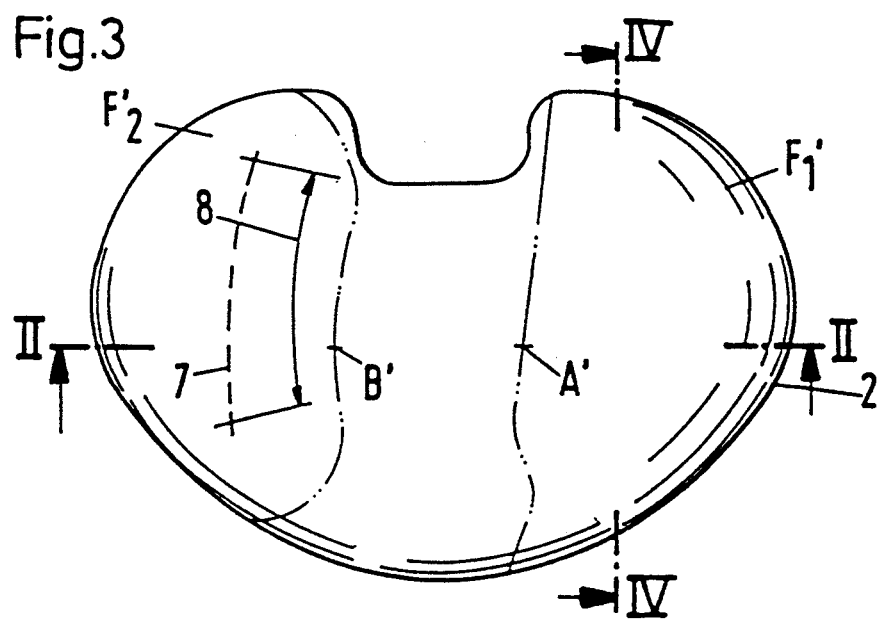
FIG. 3 is a plan view of the guide surfaces of the tibial part.

As shown in FIG. 1 the medial guide surface $F_1'$ of the tibial part is a plane surface, which is perpendicular to the tibia axis 3, while the track 7 of the lateral guide surface $F_2'$ also lies in a plane perpendicular to the tibia axis 3 and in this plane comprises a curvature by a critical angle 8 of 20° in the lateral direction so as to enable an internal rotation of the tibial part 2 about the tibia axis 3. The generatrix for the lateral guide surfaces is a segment of a circle with a radius $R_3$, which in the case of the tibial part 2 is guided along the track 7 and which in the case of the femoral part 1 for a determined angle of flexure comprises the same axis of rotation 5 for its radius $R_n$, which follows track 7, and also for its general points with radius $R_2$, as the medial guide surface $F_1$ with radius $R_1$.

On the tibia side a type of eminentia is formed in a transition zone 4 between the limit points A, A' of the medial guide and the limit points B, B' of the lateral zone. Here the gradient constantly changes from the medial to the lateral direction, so that between femoral part 1 and tibial part 2 a space 6 is produced, which permits relative rotational movement over critical angle 8.

Figure 4:
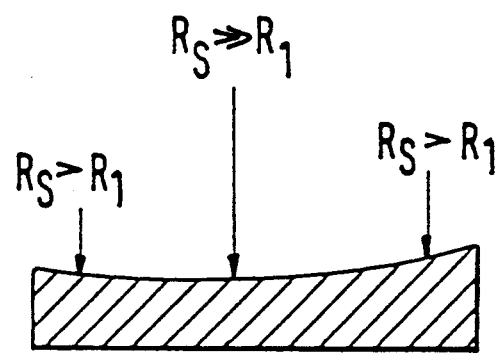
FIG. 4 is a sagittal section through a tibial part corresponding to the one shown in FIG. 1 and is taken on line IV—IV of FIG. 3.

The sagittal section of FIG. 4 shows that the plane $F_1$ and the track 7 lying in a plane parallel thereto progress into a raised edge in the sagittal edge region of the tibial part 2, with the radius of curvature $R_s > R_1$ or $R_s > R_n$, respectively. This edge region forms a limiting guide for the femoral part 2. The central region provided for the translation does not need to be absolutely flat. It can have a slight curvature with a radius $R_s$ that is a multiple of the radii $R_1$ or $R_n$ of the guide surfaces $F_1$, $F_2$ of the femoral part

What is claimed is:

1. An artificial knee joint comprising a convex femoral part which comprises smaller radii of curvature as flexure increases (1) and a tibial part (2), which performs a rolling and sliding movement, the femoral part (1) and the tibial part (2) each comprising a lateral guide surface ($F_2$, $F_2'$) and a medial guide surface ($F_1$, $F_1'$), the medial guide surface ($F_1'$) of the tibial part forming a flat guide plane, which at different flex angles abuts cylindrical guide surface ($F_1$) of the femoral part with line contact, the lateral guide surface ($F_2'$) of the tibial part being trapped by a lateral condyle with different flex angles in a frontal plane through line contact along circular segments having a common radius of curvature ($R_3$) and forming a track (7) in a plane parallel to the medial guide surface ($F_1'$), a magnitude of the radius of curvature ($R_3$) being between a smallest one and a largest one of radii of curvature ($R_n$) of the lateral guide surface ($F_2$) in a sagittal plane, with ($R_n$) being a radius which extends in the track (7), and including a transition zone (4) extending in a transversal direction between the lateral and medial guide surfaces ($F_2'$, $F_1'$) of the tibial part (2) with a gradient from an end point (B') of the lateral guide surface to an end point (A') of the medial guide surface forming a continually changing type of eminentia therebetween.

2. An artificial knee joint according to claim 1, wherein the track (7) of the lateral guide surface ($F_2'$) of the tibial part (2) comprises a curvature about an axis (3), which during relative flexure of the femoral part (1) enables an internal rotation of the tibial part (2) about the axis (3).

3. An artificial knee joint according to claim 2, wherein in a non-twisted position the femoral part (1) is at a distance from the transition zone (4) of the tibial part (2) permitting relative rotational movement of the tibial part (2) about the axis (3) up to a critical angle (8).

4. An artificial knee joint according to claim 3, wherein rotation of the tibial part (2) about the axis (3) is attainable up to a critical angle (8) of 20°.

5. An artificial knee joint according to claim 1, wherein the flat guide plane ($F_1'$) and the track (7) lying in a parallel plane thereto comprise a slight curvature with a final radius of curvature ($R_s$) which is a multiple of the radii of curvature ($R_1$, $R_n$) of the guide surfaces ($F_1$, $F_2$) of the femoral part (1).

6. An artificial knee joint according to claim 5, wherein radii of curvature ($R_s$) in the sagittal plane decrease towards an edge of the tibial part (2) and are larger than the radii of curvature ($R_1$, $R_n$) of the guide surfaces.

7. An artificial knee joint comprising a femoral part and a cooperating tibial part, the femoral part and the tibial part each including a lateral guide surface and a medial guide surface, the medial guide surface of the tibial part forming a flat guide plane, the medial guide surface of the femoral part being generally cylindrical and being defined by radii of curvature which decrease as relative flexure between the parts increases so that during flexure of the parts the medial guide surface of the tibial part makes line contact with the cylindrical guide surface of the femoral part, the lateral guide surface of the tibial part being concave and the cooperating lateral guide surface of the femoral part being convex, at different flex angles between the parts the lateral guide surfaces of the parts being in line contact along circular segments having a common radius of curvature and forming a track in a plane parallel to the medial guide surface of the tibial part, the radius of curvature being between a smallest one and a largest one of radii of curvature of the lateral guide surface of the femoral part in a sagittal plane, and a transition zone between the lateral and medial guide surfaces of the tibial part forming a gradient between proximate ends of the lateral guide surface and the medial guide surface to define a continually changing eminentia therebetween which limits relative rotational movements of the parts about a tibial axis of the tibial part.

* * * * *